US006882701B2

(12) United States Patent
Ferrandino et al.

(10) Patent No.: US 6,882,701 B2
(45) Date of Patent: Apr. 19, 2005

(54) X-RAY FLUORESCENCE SYSTEM AND METHOD

(75) Inventors: Frank H. Ferrandino, Ronkonkoma, NY (US); Weimin Si, Stony Brook, NY (US); Douglas S. Holmes, Centereach, NY (US); Harvey T. Stone, Forest Hills, NY (US)

(73) Assignee: Thermo Noran, Inc., Middleton, WI (US)

( * ) Notice: Subject to any disclaimer, the term of this patent is extended or adjusted under 35 U.S.C. 154(b) by 0 days.

(21) Appl. No.: 10/024,064

(22) Filed: Dec. 18, 2001

(65) Prior Publication Data

US 2002/0057759 A1 May 16, 2002

Related U.S. Application Data

(62) Division of application No. 09/395,523, filed on Sep. 14, 1999, now Pat. No. 6,345,086.

(51) Int. Cl.[7] .......................................... G01N 23/223
(52) U.S. Cl. ........................................ 378/44; 378/45
(58) Field of Search ............................. 378/44, 45, 84, 378/85, 145, 147, 203, 160, 161, 43

(56) References Cited

U.S. PATENT DOCUMENTS

| | | | |
|---|---|---|---|
| 3,143,651 A | * | 8/1964 | Giacconi et al. ............ 378/147 |
| 4,539,695 A | * | 9/1985 | La Fiandra ................... 378/34 |
| 4,597,093 A | | 6/1986 | Fischer ......................... 378/50 |
| 4,648,107 A | | 3/1987 | Latter ........................... 378/50 |
| 4,780,903 A | | 10/1988 | Soezima ...................... 378/145 |
| 4,821,301 A | | 4/1989 | Cocks .......................... 378/70 |
| 4,860,329 A | | 8/1989 | Weiser et al. ................. 378/50 |
| 4,866,747 A | | 9/1989 | Wartburg ...................... 378/50 |
| 4,916,720 A | | 4/1990 | Yamamoto et al. ........... 378/81 |
| 4,962,518 A | | 10/1990 | Spongr et al. ................ 378/50 |

(Continued)

Primary Examiner—Craig E. Church
Assistant Examiner—Jurie Yun
(74) Attorney, Agent, or Firm—Morgan & Finnegan, LLP

(57) ABSTRACT

The invention provides a system and method for microscopic X-ray fluorescence. An X-ray source, X-ray focusing element and a tapered X-ray opaque focusing aperture provide a focused X-ray spot on a sample. The system translates a sample between an imaging position and a testing position. In the imaging position, the sample is aligned in three dimensions and after alignment, the system automatically translates the sample between the imaging position and the testing position. To avoid collision between the sample and other elements of the system, a position detecting device terminates the sample translation if the sample trips the position detecting device. The focusing aperture of the system has a tapered through opening to block unfocused X-rays and reduce or eliminate a halo effect. To detect low atomic number elements, a detector aperture is vacuum sealed to an X-ray detector and X-ray elements of the system are vacuum evacuated.

31 Claims, 10 Drawing Sheets

U.S. PATENT DOCUMENTS

| | | | |
|---|---|---|---|
| 5,001,737 A | | 3/1991 | Lewis et al. .................. 378/147 |
| 5,029,337 A | | 7/1991 | MacKenzie et al. ........... 378/90 |
| 5,033,074 A | * | 7/1991 | Cotter et al. .................. 378/140 |
| 5,060,247 A | | 10/1991 | Watanabe ..................... 378/50 |
| 5,062,127 A | | 10/1991 | Sayama et al. ................ 378/45 |
| 5,077,766 A | | 12/1991 | Schwenke et al. ............. 378/45 |
| 5,101,422 A | | 3/1992 | Thiel et al. ................... 378/145 |
| 5,103,470 A | | 4/1992 | Iwamoto ....................... 378/45 |
| 5,192,869 A | | 3/1993 | Kumakhov ............... 250/505.1 |
| 5,199,057 A | * | 3/1993 | Tamura et al. ................. 378/43 |
| 5,309,495 A | | 5/1994 | Fischer ......................... 378/89 |
| 5,365,563 A | | 11/1994 | Kira et al. ..................... 378/48 |
| 5,418,826 A | | 5/1995 | Sato et al. ..................... 378/48 |
| 5,428,656 A | | 6/1995 | Kira et al. ..................... 378/45 |
| 5,491,737 A | * | 2/1996 | Yarnall et al. ................. 378/58 |
| 5,497,008 A | | 3/1996 | Kumakhov ............... 250/505.1 |
| 5,511,103 A | * | 4/1996 | Hasegawa ..................... 378/44 |
| 5,570,406 A | | 10/1996 | Komatani ..................... 378/44 |
| 5,570,408 A | | 10/1996 | Gibson et al. ................. 378/84 |
| 5,604,353 A | | 2/1997 | Gibson et al. ................. 378/149 |
| 5,633,908 A | | 5/1997 | Rindby et al. ................. 378/145 |
| 5,732,120 A | | 3/1998 | Shoji et al. .................... 378/45 |
| 5,745,547 A | | 4/1998 | Xiao ............................. 378/145 |
| 5,747,821 A | | 5/1998 | York et al. .................... 378/145 |
| 5,847,388 A | * | 12/1998 | Foote et al. ................... 250/310 |
| 5,848,119 A | * | 12/1998 | Miyake et al. ................. 378/34 |
| 5,937,026 A | * | 8/1999 | Satoh ............................ 378/44 |
| 6,108,398 A | * | 8/2000 | Mazor et al. .................. 378/145 |
| 6,226,349 B1 | * | 5/2001 | Schuster et al. ............... 378/81 |
| 6,295,334 B1 | * | 9/2001 | Toyota .......................... 378/145 |

\* cited by examiner

TRANSLATION

X-RAY FLUORESCENCE SYSTEM AND METHOD

This is divisional of application Ser. No. 09/395,523, filed Sep. 14, 1999, now U.S. Pat. No. 6,345,086.

BACKGROUND OF THE INVENTION

1. Field of the Invention

The invention is directed to X-ray fluorescence systems and methods. More particularly, the invention is directed to microscopic X-ray fluorescence with focused X-ray beams.

2. Background Information

Most, if not all atomic elements will fluoresce when illuminated with X-ray energy. The resulting fluorescence spectrum is generally characteristic of the element. In the microelectronics manufacturing field, X-ray fluorescence is used to determine both the presence of elements and with appropriate conditions, the concentration of different elements in deposited layers. Under appropriate conditions, it is also possible to determine layer depths in microelectronics devices using X-ray fluorescence.

Quantitative analysis of the resulting X-ray fluorescence is frequently performed with a technique called fundamental parameters. Typically, analysis of X-ray fluorescence by the fundamental parameters technique uses the spectrum of fluorescence wavelengths and the relative intensities in that spectrum.

Given the analytic capabilities of X-ray fluorescence, and the decreasing size of features on microelectronics devices, microscopic X-ray fluorescence techniques were developed. However, in contrast to optical methods, X-rays are not easily susceptible to the known techniques of optical refraction using a lens. Thus, for applications where a low level of X-ray energy in a small or focused area is sufficient, systems use a high-power X-ray source and a pin-hole or very small aperture to provide X-ray illumination of the small area. However, this is inefficient and does not allow higher X-ray energy without significant and impractical increases in X-ray power. Therefore, techniques to focus X-rays are advantageous and have been developed. One such technique is the capillary optics technique. However, capillary optics for X-ray systems are known to produce a halo effect. Systems to eliminate or reduce the halo effect of an X-ray focusing system are needed.

The known microscopic X-ray fluorescence systems are less sensitive to low atomic number elements and are unable to detect elements below certain numbers. Systems and methods to detect lower atomic number elements are needed.

As the feature size on microelectronic devices decreases and focused X-ray systems generate smaller X-ray spots, it becomes hard to accurately locate particular features on a sample and then accurately position the focused X-ray spot on that particular feature. Systems and methods to accurately and reliably locate small features and position an X-ray spot on the feature are needed.

When X-ray fluorescence systems translate microelectronics wafers during the testing, it is possible that as a result of irregularities, the sample is not uniform or is improperly mounted and the sample contacts parts of the system. These collisions frequently destroy the sample and may damage or destroy parts of the system. Systems and methods to avoid contact between sample and system are needed.

SUMMARY OF THE INVENTION

The invention is directed to methods and systems of X-ray fluorescence, which are used to measure film thickness and perform analysis on the material composition of microelectronics. In one aspect, the invention provides an X-ray fluorescence system comprising an X-ray source; an X-ray focusing element with an input and an output end, the input end in proximity to the X-ray source; and an aperture disposed on the output end of the focusing element so as to substantially block unfocused X-rays, while allowing substantially complete transmission of focused X-rays. An object and advantage of this aspect is reduction or elimination of a halo effect in focused X-ray optic systems.

In another aspect, the invention provides an X-ray fluorescence system comprising an X-ray source, the source arranged to direct X-rays substantially perpendicular to a sample in a testing position; an imaging device for imaging the sample in a viewing position; and an automatic translation device cooperating with the imaging device and the X-ray source to translate between the viewing position and the testing position. An object and advantage of this aspect is to provide accurate location and positioning of an X-ray spot on a particular feature of a sample.

In another aspect, the invention provides an X-ray fluorescence system comprising an X-ray focusing element with an input end and an output end; an aperture disposed on the output end of the focusing element; and a vacuum source connectable to the X-ray focusing element for evacuating the X-ray focusing element. The X-ray detector is also connectable to a vacuum source. The sample remains at atmospheric pressure. An object and advantage of this aspect is to provide a system to detect low atomic number elements at production rates.

In another aspect, the invention provides a method for detecting elements with low atomic numbers in an X-ray fluorescence system comprising: positioning a sample for X-ray illumination by the X-ray fluorescence system; evacuating an X-ray focusing element with a vacuum source; and illuminating the sample with X-rays focused by the X-ray focusing element while the sample remains at atmospheric pressure. The X-ray detector may also be evacuated. An object and advantage of this aspect is to provide a method to detect low atomic number elements, at production rates. Higher through-put is enhanced by eliminating the need to vacuum cycle the sample chamber.

The foregoing specific objects and advantages of the invention are illustrative of those which can be achieved by the present invention and are not intended to be exhaustive or limiting of the possible advantages that can be realized. Thus, the objects and advantages of this invention will be apparent from the description herein or can be learned from practicing the invention, both as embodied herein or as modified in view of any variations which may be apparent to those skilled in the art. Accordingly the present invention resides in the novel parts, constructions, arrangements, combinations and improvements herein shown and described.

BRIEF DESCRIPTION OF THE FIGURES

The foregoing features and other aspects of the invention are explained in the following description taken in conjunction with the accompanying drawings wherein.

It is understood that the drawings are for illustration only and are not limiting.

DETAILED DESCRIPTION OF THE INVENTION

Figure 1:
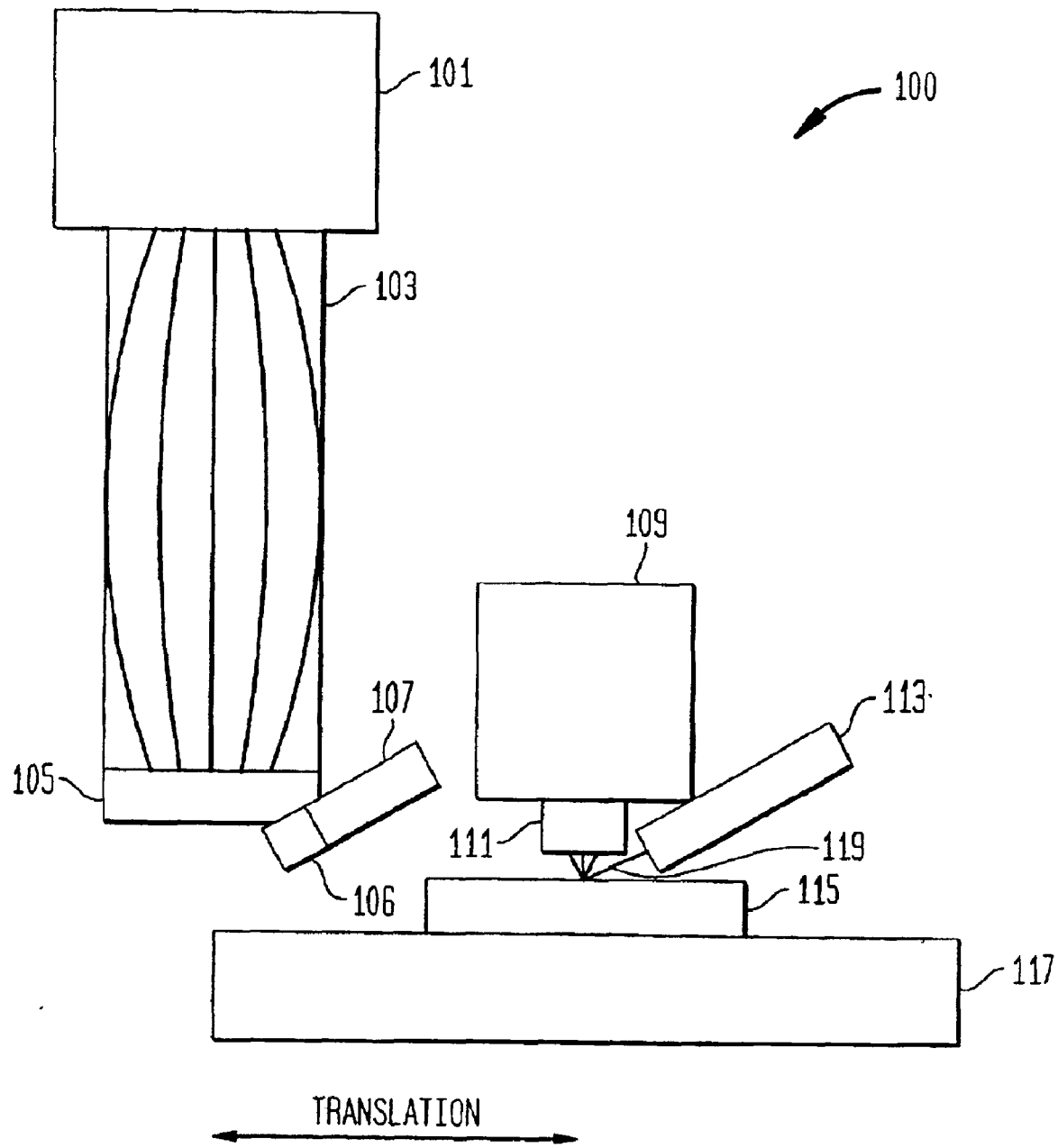
FIG. 1 illustrates an embodiment of the system in a viewing position.

An embodiment of system 100, according to the present invention, is illustrated in FIG. 1. System 100 includes an X-ray source 101, an X-ray focusing element 103, a focusing aperture 105, a detector aperture 106, and an X-ray fluorescence detector 107. System 100 further includes imaging device 109 with associated focusing optics 111 that cooperate with a distance determining device 113, that is preferably a laser device to produce a laser beam 119 and associated laser spot. System 100 further includes sample mount 117, on which sample 115 is detachably mounted. Preferably, sample 115 is detachably fastened to sample mount 117 with a vacuum mounting to allow easy of mount and unmount while reducing the risk of damage to sample 115. Sample 115 is typically a microelectronics wafer, though any sample is appropriate to the invention.

An X-ray source such as manufactured by Oxford is a suitable X-ray source 101 for system 100. An X-ray focusing element such as the polycapillary optics manufactured by X-ray Optical Systems (XOS) is a suitable X-ray focusing element 103 for system 100. An X-ray detector such as manufactured by Princeton Gamma Tech. (PGT) is a suitable X-ray detector 107 for system 100. A lens assembly such as manufactured by Optem is a suitable focusing optics 111 for system 100. Though not specifically illustrated in FIGS. 1 and 2, a translation system such manufactured by Thompson is a suitable translation system for system 100.

Alignment in Two Dimensions

Figure 2:
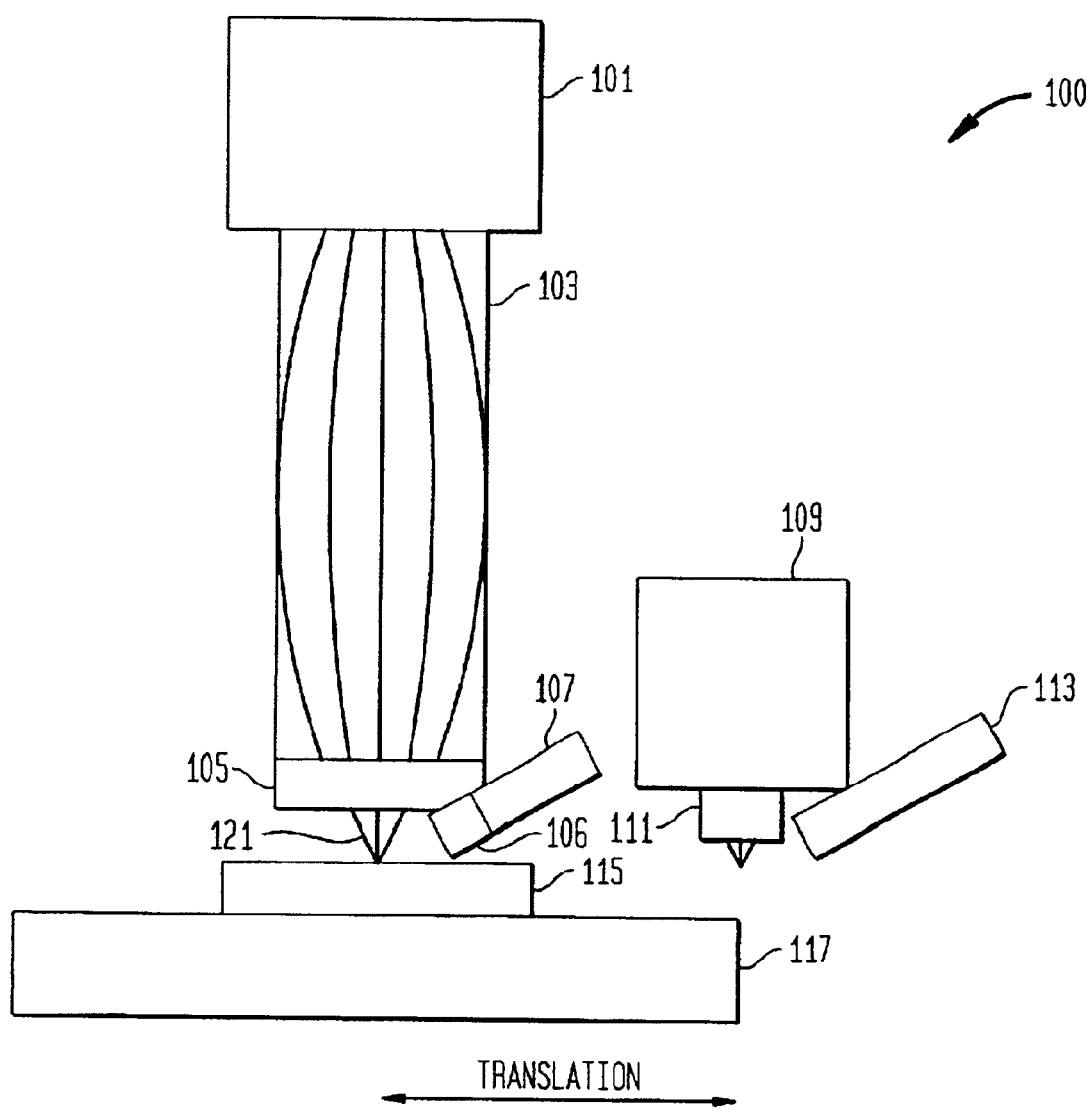
FIG. 2 illustrates an embodiment of the system in a testing position.
Figure 3:
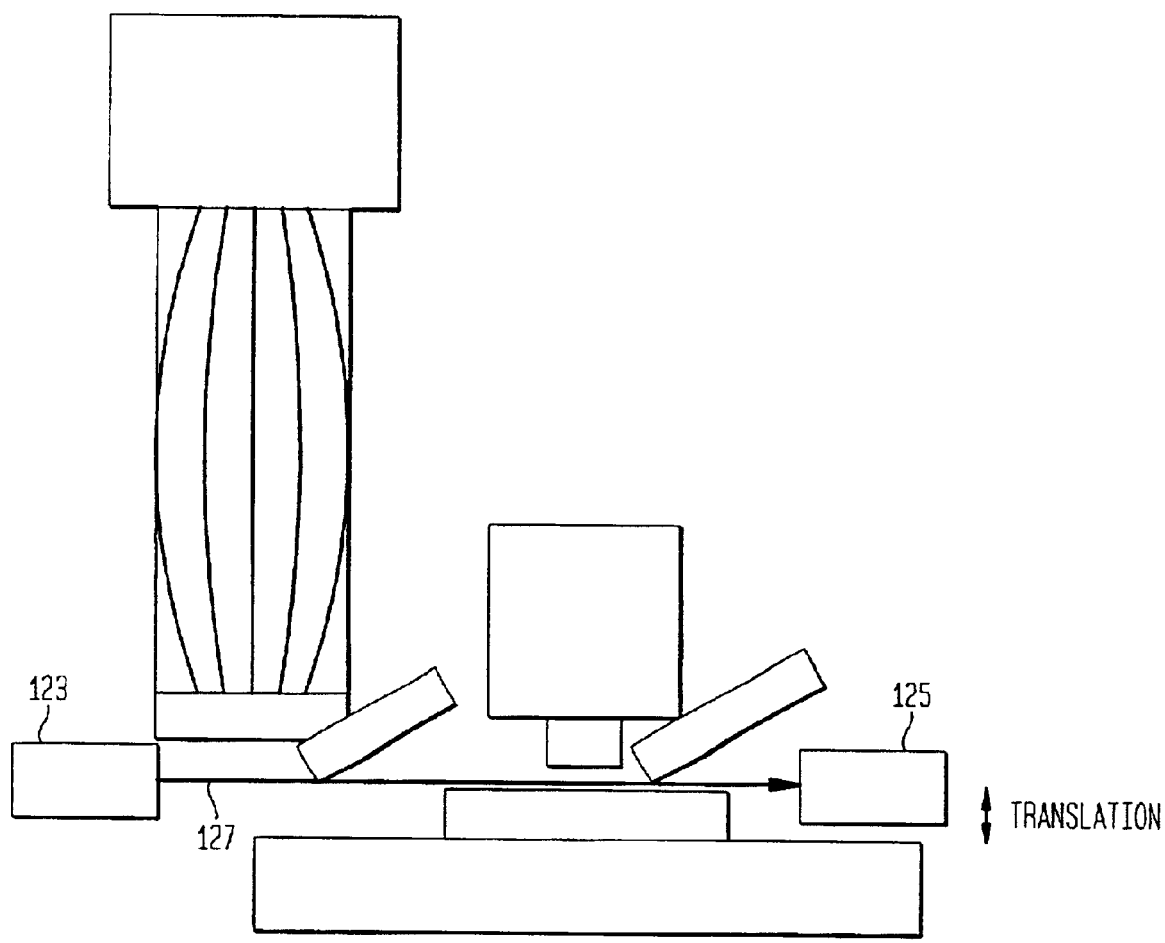
FIG. 3 illustrates a position detecting device in an embodiment of the system.

Sample mount 117 is translatable relative to the X-ray elements 101, 103, 105, 107 and the imaging elements 109, 111, 113. Two positions for the translation are an imaging position and a testing position. FIG. 1 illustrates system 100 in an imaging position, and FIG. 2 illustrates system 100 in a testing position.

Translation of sample 115 and sample mount 117 between the imaging position and the testing position is accomplished with low hysteresis or low back-lash mechanical devices. The translation mechanism is computer controlled in three dimensions and accurately and repeatedly positions sample 115 as close as about ±5 microns of a desired position. The majority of system 100 translation occurs in two dimensions that are substantially in the plane of sample 115. However, system 100 also translates sample 115 in the third dimension normal to sample 115. In this manner, sample 115 is accurately and repeatably translated between the imaging position (FIG. 1) and the testing position (FIG. 2).

With system 100 in the imaging position, as illustrated in FIG. 1, sample 115 is located in the field of view of focusing optics 111. In the imaging position, imaging device 109 generates a magnified video or digital image of an area on sample 115. This area of sample 115 is magnified by focusing optics 111 and the resulting image is further manipulated by processing circuitry of imaging device 109. Typically, imaging device 109 and focusing optics 111 generate an image magnification between 30x and 300x of sample 115. With this magnification, an operator or automated image processing system can detect and differentiate between features at least as small as 10 microns on a sample.

Laser 113 is calibrated and then fixed relative to image elements 109 and 111. Laser 113 is oriented off-axis from the imaging axis of imaging device 109 and focusing optics 111. As a result, when sample mount 117 and sample 115 are moved in and out of the focal plane of focusing optics 111 (i.e., normal to sample 115), a laser spot from laser 113 moves horizontally across the field of view displayed by imaging device 109. Alignment in this third dimension is described in greater detail below with reference to FIG. 7.

Referring to FIG. 2, system 100 is illustrated in a testing position. In a testing position, sample mount 117 and sample 115 are aligned with a focused X-ray spot that is generated by X-ray source 101, X-ray focusing element 103 and focus aperture 105. In the testing position, the focused X-ray spot illuminates or is concentrated on a small area of sample 115. As a result of the X-ray illumination, atomic elements that comprise sample 115 fluoresce according to known physical properties. This fluorescence is detected by X-ray fluorescence detector 107, which is oriented off-axis from the focused X-ray spot. Detector aperture 106 provides enhanced detection of low atomic number elements, as described in greater detail below. As illustrated in FIG. 2, X-ray elements 101, 103, 105 are oriented substantially normal (i.e., perpendicular) to the planar surface of sample 115. With a focused X-ray system, normal or perpendicular orientation is preferred, because the X-ray spot remains in the same location on the sample as the sample is moved in and out of the focal plane. If the X-ray source is off-normal, the X-ray spot will move horizontally on the sample as the sample is moved in and out of the focal plane. This horizontal movement of the X-ray spot introduces further complexity for accurate positioning and is not desirable. In addition, normal projection of the X-ray spot will minimize size (i.e., diameter) of the X-ray spot, whereas angled (off-normal) projection will produce a larger elongate, or oval spot. Movement of sample 115 in and out of the focal plane is part of alignment in the third dimension, explained in greater detail below.

X-ray focusing element 103 of system 100 produces an X-ray spot that is typically about 37 microns in radius (i.e., 75 microns in diameter), though the spot size may be smaller. The X-ray spot contains a majority of the X-ray energy, and for the purposes of the specification and claims, the X-ray spot in a focused X-ray system is defined as the focused area on the sample that contains approximately 90% or more of the X-ray energy illuminating the sample. However, X-ray spot size does vary according to the elements measured and can range from 40 to 125 microns depending on the energy of fluorescence detected from the sample elements. Accurate three dimensional alignment and orientation of the X-ray spot and features on sample 115 is important, especially as the feature size decreases to the size of the X-ray spot.

Referring to FIG. 8, different configurations and orientations of an X-ray spot and a feature on a sample are illustrated, as viewed in two dimensions from the perspective of X-ray source 101. In FIG. 8A, feature 801, located on sample 115, is illustrated as a square feature, with dimensions 2R by 2R. In FIG. 8A, a focused X-ray spot, with a radius R is overlayed on feature 801. When the centers of focused X-ray spot 803 and feature 801 are aligned, the spot is completely over the feature and only feature 801 is illuminated by spot 803.

Figure 8A:
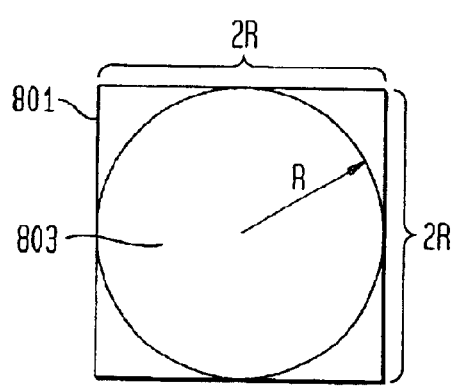
FIG. 8 illustrates alignment of X-ray spot and feature for different spot sizes.
Figure 8B:
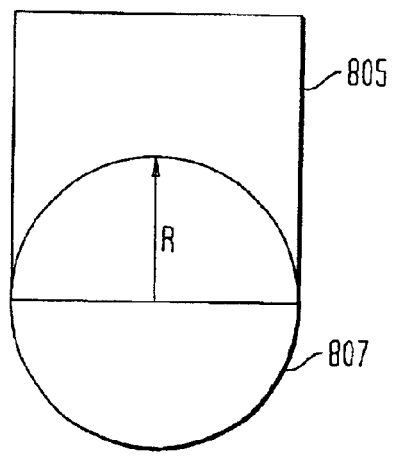

In FIG. 8B, which illustrates the same size feature and spot of FIG. 8A, feature 805 is misaligned with respect to spot 807 by radius R. In this configuration, one half of the X-ray energy of spot 807 falls on feature 805 and one half of the X-ray energy of spot 807 falls off feature 805. Thus, when the feature on sample 115 and the focused X-ray spot are similarly sized, as illustrated in FIGS. 8A and 8B, misalignment can result in significant errors.

Figure 8C:
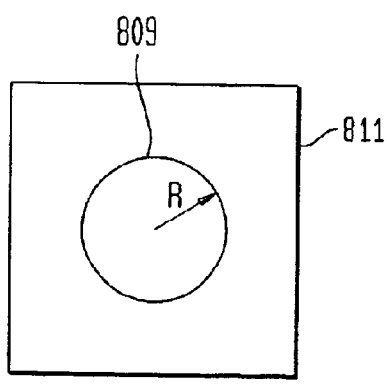
Figure 8D:
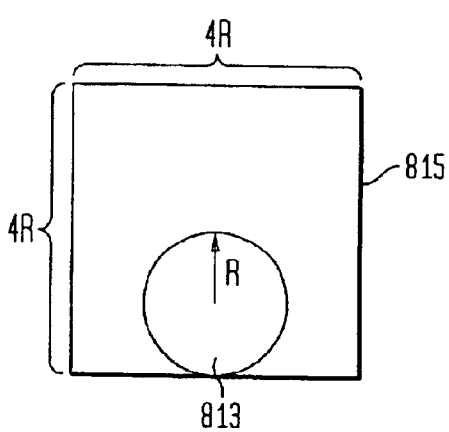

As illustrated in FIGS. 8C and 8D, when the focused X-ray spot size is smaller than the feature size, there is greater tolerance for misalignment. In FIG. 8C, centers of spot 809 and feature 811 are aligned. In FIG. 8D, spot 813 and feature 815 are misaligned by radius R. In the examples of FIGS. 8C and 8D, square features 811, 815 have dimensions 4R by 4R, and even when the focused X-ray spot and the feature are misaligned by radius R, the focused X-ray spot remains on the feature of the sample.

It is thus apparent that as the focused X-ray spot size approaches the feature size, alignment of the spot with the feature is very critical and becomes more difficult. However, as the feature size on samples and the focused X-ray spot sizes become smaller, it becomes harder to locate a particular feature or position on a sample, and then accurately and repeatably place a focused X-ray spot on that feature or position. System 100 of the present invention assists with that repeatable location and placement.

In one embodiment of system 100, X-ray elements 101, 103, 105, 106 and 107 are suitably aligned with each other and then rigidly fixed with respect to each other. Similarly, imaging elements 109, 111 and 113 are also suitably aligned with each other and then rigidly fixed with respect to each other. After the X-ray elements and the imaging elements are properly aligned and fixed in position, they are aligned to each other and then rigidly fixed with respect to each other in system 100. Once thus aligned and rigidly fixed as parts of system 100, there is little opportunity for X-ray elements 101, 103, 105, 106 and 107 to move relative to imaging elements 109, 111 and 113. As a result, it is possible to accurately determine a precise three dimensional relationship between the position of the focused X-ray spot produced by the X-ray elements and the center of the optical field of view of the imaging elements. Once this three dimensional relationship is precisely determined, it is then possible to program a computer controlled translation device to move accurately and repeatably between a viewing position and a testing position. In the viewing position, a particular point or feature of sample 115 is aligned in two dimensions with a calibrated center of the field of view produced by imaging device 109. This is accomplished by observing a calibrated video or digital image produced by imaging device 109 and using cursor or joy-stick control to move sample 115 relative to imaging device 109 in two dimensions until a reticle or cross-hair is centered on the desired feature or position. The image presented to an operator resembles the presentation in FIG. 8, with the superimposed X-ray spot. Once positioned in two dimensions, the prior calibration and computer control between viewing position and testing position allows system 100 to automatically translate sample 115 into proper alignment with the focused X-ray spot.

Alignment in a Third Dimension

The system described thus far provides an accurate and repeatable two dimensional position and translation system, which facilitates positioning in two dimensions. However, accurate positioning in the third dimension is not easily performed with the technique thus described. To properly position the sample in the third dimension, system 100 uses a distance measuring device, 113. In one embodiment, distance measuring device 113 is an off-axis laser that allows precise positioning in the third dimension.

Figure 9:
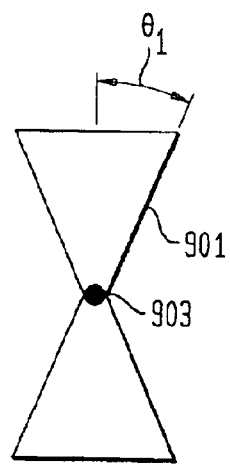
FIG. 9 illustrates a focused X-ray spot as viewed parallel to the sample plane.

Before describing the positioning system in the third dimension, a focused X-ray system, as viewed parallel to the plane of sample 115, is illustrated in FIG. 9. As illustrated, because of physical limitations of X-ray source 101 and X-ray focusing element 103, the focused X-ray beam 901 converges to a spot, not a point. Within the spot, there may be variation of X-ray energy, but the majority of the X-ray energy is confined within the spot. Depending on how much focusing the X-ray focusing element provides, the focusing angle $\emptyset_1$, measured normal to the sample, is small or large. With a small focusing angle $\emptyset_1$, there is little change in spot size as sample 115 moves in and out of the center of focus. However, with a larger focusing angle, there will be greater change in spot size as sample 115 moves in and out of the center of focus. As illustrated in FIG. 9, it is thus desirable to align the focused X-ray spot with the feature on sample 115 within about the same accuracy 903 in all three dimensions (i.e., within about the radius of the focused X-ray spot).

Figure 7A:
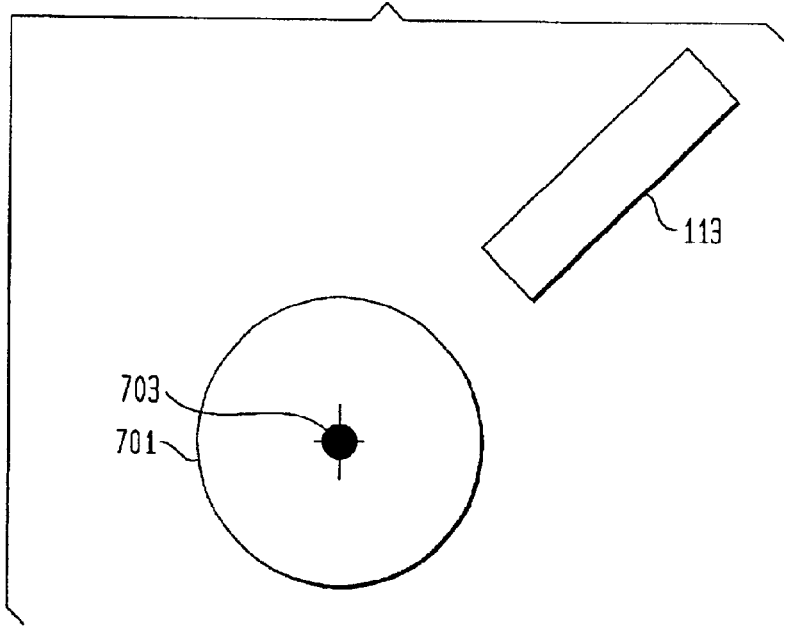
FIG. 7 illustrates an embodiment of a distance determining device of the system.
Figure 7B:
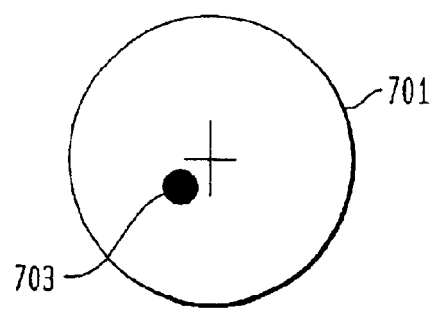
Figure 7C:
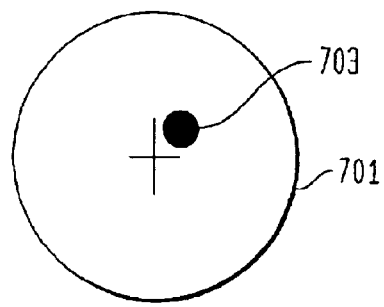

System 100 uses laser 113 in conjunction with imaging elements 109, 111 to align the focused X-ray spot and the feature in the third dimension within the desired accuracy. This technique is illustrated in FIG. 7. An image 701 of a portion of sample 115, as provided by imaging device 109 is provided in FIG. 7A. Located off-axis, laser 113 directs a laser beam into the field of view of imaging device 109. The laser spot 703 illuminates the surface of sample 115 and is observable using imaging device 109. As illustrated in FIG. 7A, laser spot 703 is centered in a cross-hair or reticle of imaging device 109. When sample 115 is properly aligned in the third dimension, an image similar to FIG. 7A is presented on an image display. When sample 115 is below the focal plane, laser spot 703 falls on the surface of sample 115 at a different location, owning to the off-axis alignment of laser 113. FIG. 7B illustrates the position of laser spot 703 when sample 115 is below the focal plane. Similarly, when sample 115 is above the focal plane, laser spot 703 illuminates the surface of sample 115 at a different position. FIG. 7C illustrates laser spot 703 on the surface of sample 115 when sample 115 is above the focal plane. As illustrated in FIG. 7, it is possible to accurately observe whether sample 115 is properly positioned within the focal plane of the focused X-ray spot by observing where a laser spot falls on sample 115. The proper positioning of the sample in the third dimension can be performed manually by an operator observing laser spot 703 and adjusting the sample position with cursor or joy-stick control. Alternatively, system 100 may use an automated process to position the sample in the third dimension using the laser spot.

In system 100, the three dimensional positioning and translation thus described are typically accomplished by fixedly mounting the X-ray elements and the imaging elements to system 100 and providing an accurate and calibrated translation system to automatically move sample 115 between the viewing position and the testing position.

Similarly, alignment in the viewing position is typically performed by an operator observing the features on sample 115 using imaging device 109 and aligning the sample with cursors or a joy-stick control. Alternatively, system 100 may automatically perform the alignment in the viewing position with feature recognition programs to identify the desired features and properly position the sample in all three dimensions.

Similarly, the calibration of system 100 to calculate and correlate the positional differences required for translation between the viewing position and the testing position may be manual or automatic.

Collision Avoidance Between Sample and Imaging Elements or X-ray Elements

As described above, system 100 moves sample 115 relative to other fixed elements of the system to properly position the sample within an imaging field of view, in an imaging position. After properly aligned in three dimensions at the imaging position, system 100 automatically translates the sample into a testing position. To perform this automatic translation, system 100 must have very accurate knowledge of the relationship between the imaging position and the testing position. In normal operation, all of the translation between imaging position and testing position is in two dimensions, with no translation in the third dimension.

It is possible due to sample irregularities, or carelessness by the operator that as a sample translates between the imaging position and the testing position, the sample will contact the imaging elements or the testing elements. Any contact will likely damage the sample and may destroy or damage the imaging elements or the X-ray elements. Thus, avoidance of contact between sample and other parts of system 100 is important.

Avoidance of contact between the sample and other elements of system 100 is accomplished with a position detecting device. In one embodiment, the position detecting device includes a light beam transmitter 123 which generates a light beam 127 that is received by light beam receiver 125. The position detecting device detects the sample if the translation mechanism brings the sample too close to either the X-ray elements or the imaging elements. If such a condition occurs, system 100 stops the translation of the sample. This avoids contact between sample 115 and X-ray elements 101, 103, 105, 106, 107 or imaging elements 109, 111, 113.

In one embodiment, light beam transmitter 123 is a laser, light beam 127 is a laser beam, and light beam receiver 125 is a laser detector. In another embodiment, light beam transmitter 123 is a focused infrared light emitting diode and light beam receiver 125 is an infrared detector, while light beam 127 is a focused infrared light beam. It is also possible that the position detecting device uses another form of position detection such as radio frequency energy. A key requirement in avoiding contact is that the position detecting device detect movements of sample 115 that approach X-ray elements 101, 103, 105, 106, 107 or imaging elements 109, 111, 113 before there is any contact and thereby avoid contact by stopping movement of the sample. To help avoid contact, the position detecting device cooperates with the translation mechanism of system 100 to stop translation of sample 115 if parts of the sample or sample mount break the light beam.

The Halo Effect in Focused X-ray Systems

As previously discussed, the optical properties of X-rays are not easily applied to practically control X-ray paths. Nonetheless, X-rays do behave according to known principles of light optics. One such focusing apparatus, using low angle reflection, is the X-ray capillary focusing element that is described in U.S. Pat. No. 5,192,869, to Kumakhov. Capillary optics suitable for system 100 generally produce a focused X-ray spot of about 75 microns or less.

When a capillary optics focusing element is appropriately integrated with an X-ray source and the X-ray source is energized, unfocused X-rays from the source illuminate the input end of the focusing element. Some of the illuminating X-rays enter the capillary optics and are focused by the optics. Other illuminating X-rays enter the focusing element and are not focused by the optics. The focused and unfocused X-rays emerge from the focusing element and illuminate the sample. As a result of interactions between the focused X-rays, the unfocused X-rays and the X-ray optics, the focused X-ray spot has a halo of X-ray energy around the spot.

The X-ray halo is detrimental to precise X-ray fluorescence measurements. Areas of sample 115 that are outside the focused X-ray spot will fluoresce as a result of the X-ray energy in the halo, thus producing erroneous data. This can be particularly disadvantageous as the spot size decreases to correspond to the feature sizes on sample 115. For almost all fluorescence measurements, it is desired that the focused X-ray spot is smaller than a feature size on sample 115. A small spot completely on a larger feature ensures that only the feature contributes to the fluorescence. However, if other areas or features on the sample are illuminated by the halo and fluoresce as a result, the results are less reliable.

Figure 4:
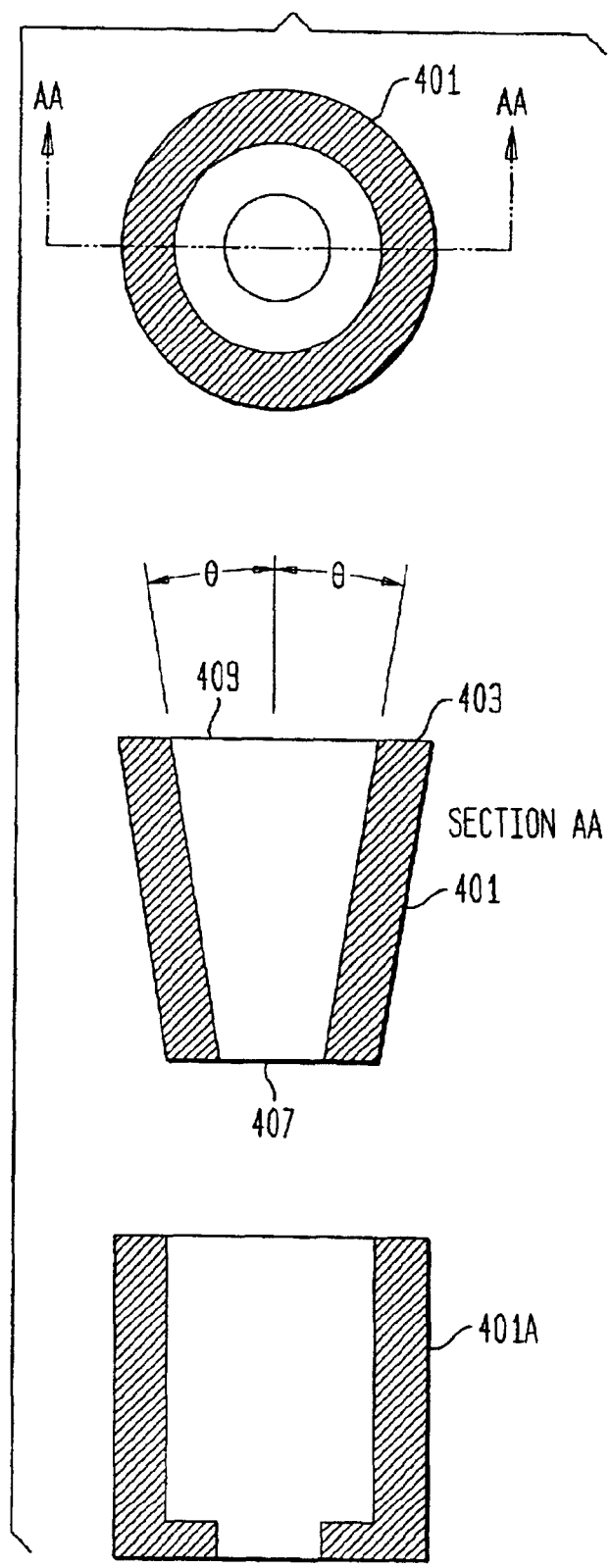
FIG. 4 illustrates an embodiment of an aperture of the system.

FIG. 4 illustrates a focusing aperture 401 that eliminates or substantially reduces this halo effect. Aperture 401 is manufactured of an X-ray opaque material, such as steel. The aperture has a tapered through opening with a wider input end 409 and an narrower output end 407. The tapered through opening has a taper angle Ø that is measured relative to the longitudinal axis of the aperture. The taper angle Ø of aperture 401 is substantially the same as the previously described focus angle $Ø_1$ of the X-ray focusing element.

When input end 409 of aperture 401 is aligned with X-ray focusing element 103, focused X-rays continue without interruption through the tapered opening. However, unfocused X-rays are blocked by face 403 of aperture 401 or attenuated when reflected by the inner face of the tapered through opening. Both reduce the undesired halo effect.

When elements in the X-ray source path are vacuum evacuated, as described below, an X-ray permeable or transparent vacuum seal covers the opening on output end 407.

In the embodiment illustrated in FIG. 4, the outer and inner surfaces of aperture 401 are tapered. However, the outer surface does not require a taper, nor does the inner surface require a taper. For example, 401A, in FIG. 4 illustrates an alternative embodiments of aperture 401 where the aperture substantially blocks unfocused X-rays, but does not have an inner or outer taper.

Detection of Low Atomic Number Elements

As the atomic number of elements in sample 115 decreases, X-ray fluorescence becomes more difficult to detect and/or less efficient. One reason for this decrease in efficiency or response is that atmospheric gases interfere with the fluorescence and attenuate the X-ray energy, or contaminate the response. One technique for increasing system sensitivity and detection of low atomic number elements is by vacuum evacuation of the entire system, including the sample. However, vacuum evacuation of the entire system is not suitable for some industrial processes where sample through-put and rapid testing is important. For these applications, detection while the sample remains at atmospheric pressure is advantageous.

In the X-ray transmission path, there are three areas that particularly benefit from vacuum evacuation. These elements are X-ray source 101, X-ray focusing element 103 and aperture 105. Also, the X-ray detection path from sample 115 through detector aperture 106 to the X-ray fluorescence detector 107 benefits from vacuum evacuation.

Figure 6A:
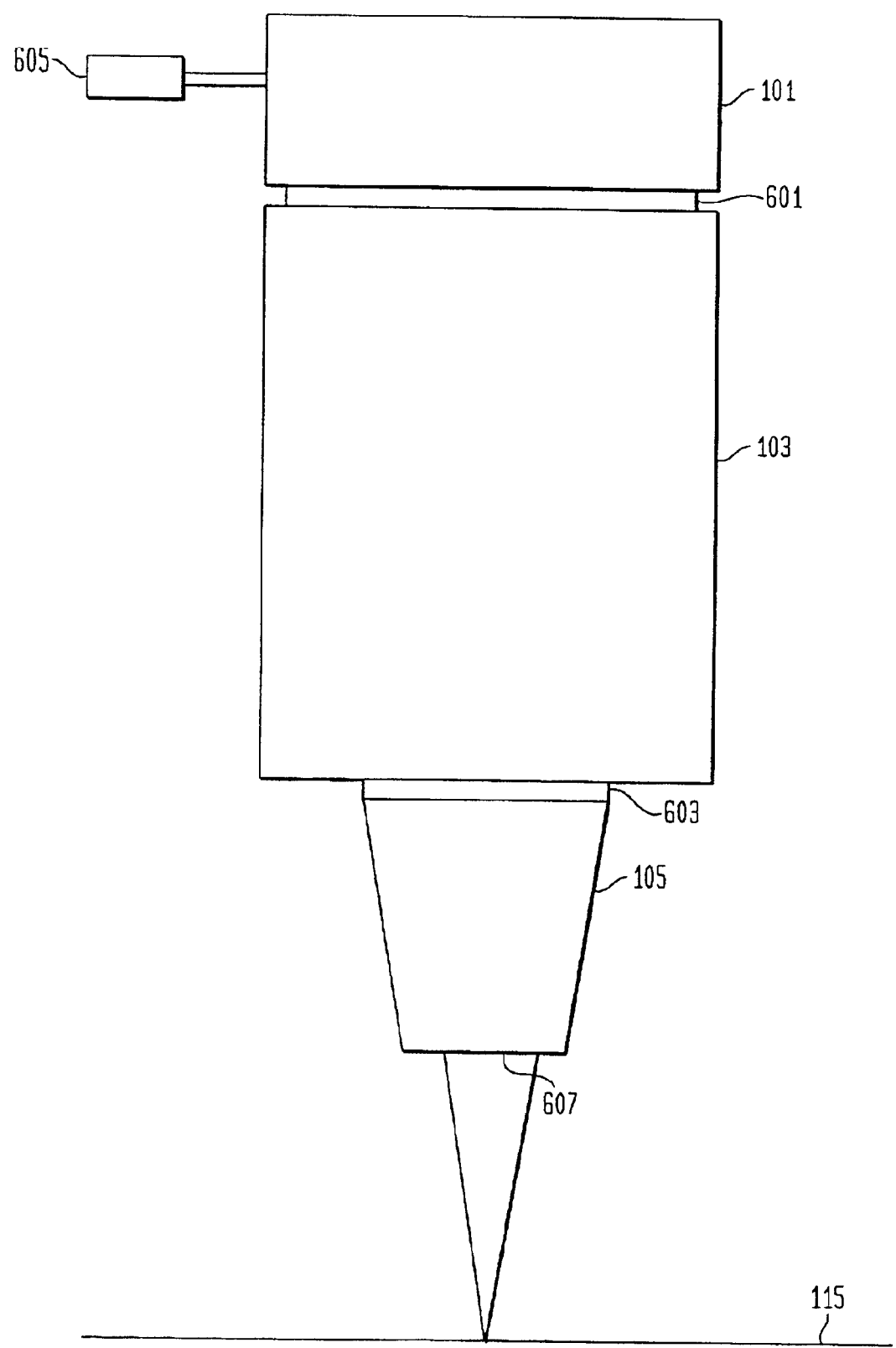
FIGS. 6A & 6B illustrate an embodiment of the system with central vacuum evacuation of elements.
Figure 6B:
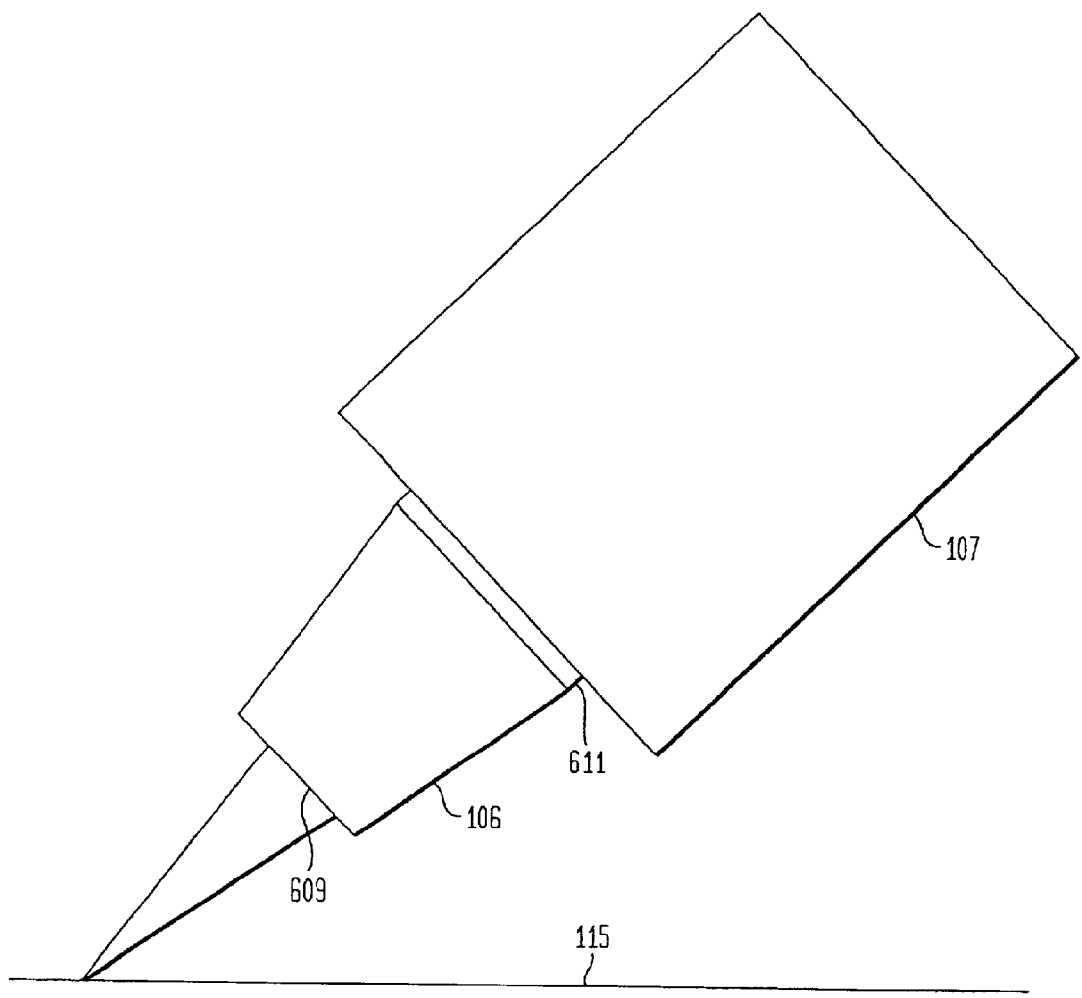

In one embodiment, illustrated in FIGS. 6A & 6B, X-ray source 101 is vacuum sealed to X-ray focusing element 103 with seal 601. X-ray focusing element 103 is vacuum sealed to aperture 105 with seal 603. The detector path includes detector aperture 106, which is sealed on one end with an X-ray permeable or transparent material and sealed on the other side to detector 107. Aperture 106 and detector 107 are both vacuum evacuated. Evacuation maintains a majority of the path from source 105 to sample 115 and sample 115 to detector 107 free from atmospheric interference.

In the configuration of FIGS. 6A & 6B, single vacuum source 605 provides vacuum evacuation of elements 101, 103, 105, 106, 107. In the configuration of FIG. 6A, an X-ray permeable or transparent vacuum seal is provided over opening 607 of aperture 105. In the configuration of FIG. 6B, another X-ray permeable or transparent vacuum seal is provided over opening 609 of aperture 106. By maintaining a vacuum of 1 milli Torr or less, in an evacuated X-ray path extending from the source through the focusing element, apertures and detector, system 100 has good sensitivity and enhanced detection of X-ray fluorescence from low atomic number elements on sample 115. The embodiment of FIGS. 6A and 6B assists in detection of elements with atomic numbers as low as Aluminum (atomic number of 13).

Figure 10:
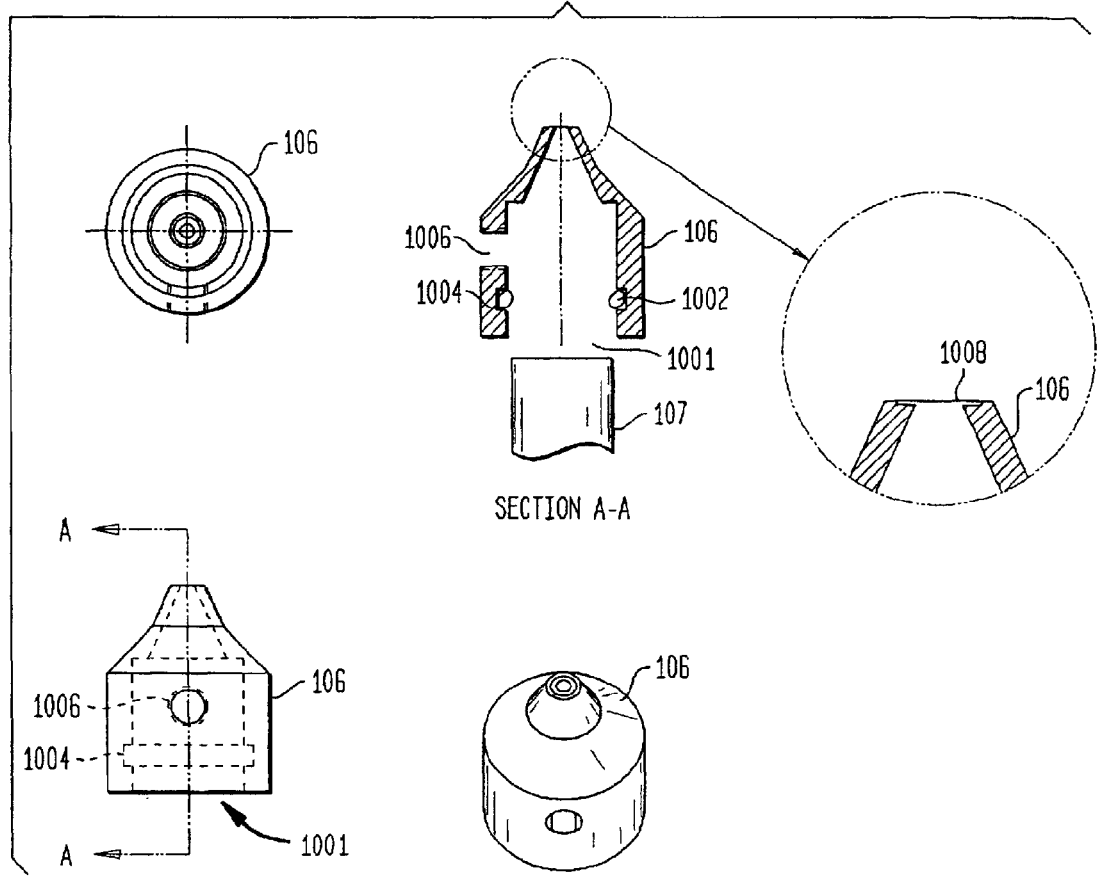
FIG. 10 illustrates an embodiment of an aperture for an X-ray detector.

FIG. 10 provides an illustration of an aperture cooperating with the X-ray detector to aid in detection of low atomic number elements. The detector aperture 106 has a conical shape and is formed of a generally X-ray opaque material, such as stainless steel. The conical shape of aperture 106 has a large opening 1001 at one end to thereby allow the aperture to cooperate with, or couple to X-ray detector 107. The coupling of the aperture to the detector includes a vacuum seal means, such as the illustrated o-ring 1002 and corresponding o-ring groove 1004. The combination of o-ring and groove helps to provide the vacuum seal between aperture 106 and detector 107. Aperture 106 also includes a port 1006 for connection of aperture 106 and a vacuum source, not illustrated.

Aperture 106 further includes an X-ray transmissive window 1008, which is sealed to aperture 106. In the preferred embodiment, the window is formed of berilium. The combination of elements allows aperture 106 to vacuum seal to detector 107, thereby providing a partially evacuated X-ray path between a sample and detector 107. This evacuated path has X-ray transmissive properties or characteristics that are different from the X-ray transmissive characteristics of the atmosphere. In a microscopic X-ray fluorescence system, this difference is primarily a reduced X-ray absorption or scattering due to atmospheric nitrogen.

It is of course possible to provide different X-ray transmissive characteristics in the X-ray path using techniques other than vacuum evacuation. For example, a gas or gas mixture with a composition different from that of the atmosphere can be introduced into aperture 106 through port 1006. If the gas has X-ray transmissive characteristics that are different from the atmosphere and thus appropriate for solution of a problem, this embodiment would similarly be part of the instant invention. It is also possible that the pressure inside aperture 106 is not below atmospheric pressure(i.e., a vacuum), but is instead equal to or above atmospheric pressure. This embodiment may be appropriate with the above-described gas.

Additionally, it may be appropriate for certain applications to have a liquid with particular X-ray transmissive properties inside aperture 106. The liquid may be maintained at any particular pressure that is appropriate.

Although illustrative embodiments have been described herein in detail, it should be noted and will be appreciated by those skilled in the art that numerous variations may be made within the scope of this invention without departing from the principle of this invention and without sacrificing its chief advantages. Such variations include mounting some or all of imaging elements 109, 111, 113 parallel to sample 115 instead of normal to sample 115. In this configuration, the image from sample 115 is reflected with a reflecting surface or mirror.

There may also be applications where sample movement is not appropriate. For these applications the translation system moves X-ray elements and imaging elements between viewing and testing positions relative to a fixed sample.

Though there is normally no translation in the third dimension, there may be instances where it is required. In those cases, the amount of translation in the third dimension depends on the difference in alignment between the imaging position and the testing position in the third dimension.

Figure 5:
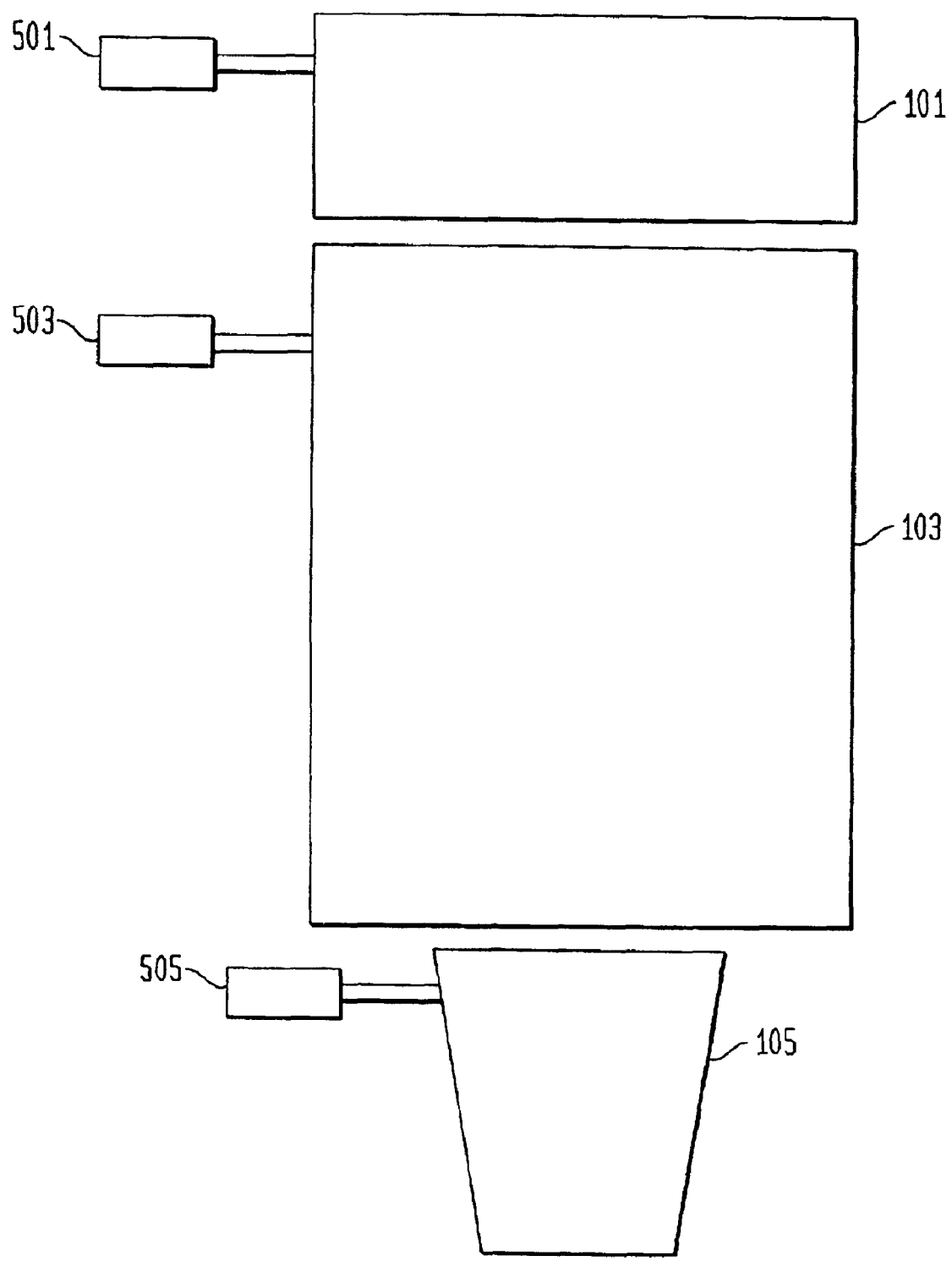
FIG. 5 illustrates an embodiment of the system with individual vacuum evacuation of individual elements.

It may be appropriate to vacuum evacuate individual elements, rather than evacuating all the elements in the X-ray path. For example, in FIG. 5, individual vacuum sources 501, 503, 505 are connected to X-ray source 101, X-ray focusing element 103 and aperture 105 respectively. In this embodiment, there is no need for a tight vacuum seal between X-ray source 101 and X-ray focusing element 103, or for a tight vacuum seal between X-ray focusing element 103 and aperture 105. Though not illustrated, individual vacuum sources could be used for detector aperture 106 and detector 107. However, with individual vacuum sources and individual elements, each element 101, 103, 105, 106, 107 must be vacuum sealed with an X-ray permeable or transparent seal.

Unless otherwise specifically stated, the terms and expressions have been used herein as terms of description and not terms of limitation. There is no intention to use the terms or expressions to exclude any equivalents of features shown and described or portions thereof and this invention should be defined in accordance with the claims that follow.

We claim:

1. An X-ray fluorescence system comprising:
   an X-ray source;
   an X-ray focusing element comprising capillary optics having an input and an output end, the input end in proximity to the X-ray source; and
   an aperture disposed on the output end of the focusing element so as to substantially block unfocused halo-producing X-rays, while allowing substantially complete transmission of focused X-rays.

2. A system according to claim 1, the aperture including a substantially X-ray opaque material.

3. A system according to claim 1, the aperture including a tapered through opening.

4. A system according to claim 3, the tapered through opening including a larger opening in proximity to the output end of the focusing element.

5. A system according to claim 3, the tapered through opening including a taper angle corresponding substantially to a focus angle of the X-ray focusing element.

6. An aperture in an X-ray fluorescence system comprising;
   a first end;
   a second end; and
   a passage connecting the first end and the second end, the first end connectable to an X-ray focusing element comprising capillary optics of the X-ray fluorescence system, the aperture to substantially block unfocused halo-producing X-rays in the X-ray fluorescence system.

7. An aperture according to claim 6, the aperture including a substantially X-ray opaque material.

8. An aperture according to claim 6, wherein the passage is a tapered passage section with a taper angle corresponding substantially to a focus angle of the X-ray focusing element.

9. An aperture according to claim 6, the aperture further comprising an X-ray transparent vacuum seal disposed at the first end or the second end.

10. An X-ray fluorescence system comprising:
    an X-ray element with a first end and a second end;
    an aperture disposed on the second end of the element;
    a vacuum source connectable to the aperture for evacuating the aperture; and
    a sample holder positioned in proximity to the aperture to hold a sample, the sample maintained at atmosphere pressure.

11. A system according to claim 10, wherein the X-ray element is an X-ray detector.

12. A system according to claim 10, wherein the X-ray element is an X-ray focusing element.

13. A system according to claim 10, wherein the aperture is vacuum sealed to the X-ray element.

14. A system according to claim 10, further comprising an X-ray source vacuum sealed to the first end of the X-ray element.

15. A system according to claim 14, further comprising a vacuum source connectable to the X-ray source for evacuating the X-ray source.

16. A system according to claim 15, wherein the vacuum source connectable to the aperture and the vacuum source connectable to the X-ray source are the same vacuum source.

17. An X-ray path in a microscopic X-ray fluorescence system, the path comprising:
- an X-ray source;
- an X-ray focusing element comprising capillary optics having an input end and an output end, the input end vacuum sealed to the X-ray source;
- a focusing aperture vacuum sealed to the second end of the focusing element so as to substantially block unfocused halo-producing X-rays, while allowing substantially complete transmission of focused X-rays; and
- a vacuum source connectable to the X-ray path for evacuating the path.

18. An X-ray fluorescence system comprising:
- a detector for detecting fluorescence from a sample to be irradiated at or around atmospheric conditions; and
- an aperture cooperating with the detector to provide an X-ray path, the X-ray path having X-ray transmissive characteristics that differ from atmospheric X-ray transmissive characteristics at or around the fluoresced sample.

19. A system according to claim 18, wherein the system is a microscopic X-ray fluorescence system.

20. A system according to claim 18, wherein the aperture has a tapered conical shape with an X-ray transmissive window.

21. A system according to claim 18, wherein the aperture is vacuum evacuable to thereby provide a vacuum evacuated X-ray path.

22. A system according to claim 18, wherein the aperture is removeable from the detector.

23. A method for detecting elements with low atomic numbers in an X-ray fluorescence system comprising:
- positioning a sample for X-ray illumination by the X-ray fluorescence system;
- evacuating an X-ray focusing element with a vacuum source;
- illuminating the sample with X-rays focused by the X-ray focusing element while the sample remains at atmospheric pressure; and
- detecting X-ray fluorescence from the illuminated sample.

24. A method according to claim 23, further comprising evacuating a focusing aperture disposed on an output end of the X-ray focusing element.

25. A method according to claim 23, further comprising evacuating an X-ray source disposed on an input end of the X-ray focusing element.

26. A method according to claim 23, further comprising evacuating an X-ray detector.

27. A method according to claim 26, further comprising evacuating a detector aperture disposed on the X-ray detector.

28. A method according to claim 23, wherein evacuating the X-ray focusing element includes evacuating to less than about 1 milli. Torr.

29. A method according to claim 23, further comprising detecting X-ray fluorescence from elements with atomic numbers above 13.

30. A method according to claim 23, wherein the focusing element comprises capillary optics.

31. An X-ray fluorescence system comprising:
- a detector; and
- an aperture cooperating with the detector to provide an X-ray path, the X-ray path having X-ray transmissive characteristics that differ from atmospheric X-ray transmissive characteristics,
- wherein a gas or gas mixture with a composition different than that of the atmosphere is provided in the X-ray path to provide the transmissive characteristics that differ from atmospheric X-ray transmissive characteristics.

* * * * *